US00PP36410P2

(12) United States Plant Patent
Bozanic Tanjga

(10) Patent No.: US PP36,410 P2
(45) Date of Patent: Jan. 28, 2025

(54) ***ROSA* PLANT NAMED 'BOZFRA321'**

(50) Latin Name: *Rosa hybrida*
Varietal Denomination: BOZFRA321

(71) Applicant: Pheno Geno Roses BV, Grubbenvorst (NL)

(72) Inventor: Biljana Bozanic Tanjga, Novi Sad (RS)

(73) Assignee: Pheno Geno Roses BV (NL)

( * ) Notice: Subject to any disclaimer, the term of this patent is extended or adjusted under 35 U.S.C. 154(b) by 0 days.

(21) Appl. No.: 18/583,398

(22) Filed: Feb. 21, 2024

(51) Int. Cl.
*A01H 5/02* (2018.01)
*A01H 6/74* (2018.01)

(52) U.S. Cl.
USPC ..... Plt./102
CPC ..... *A01H 6/749* (2018.05)

(58) Field of Classification Search
USPC ..... Plt./105, 112, 135, 146, 102, 109
CPC . A01H 5/02; A01H 5/00; A01H 6/749; A01H 6/74
See application file for complete search history.

(56) References Cited

U.S. PATENT DOCUMENTS

PP6,384 P * 11/1988 Meilland ..... Plt./108

OTHER PUBLICATIONS

Heritage Professional Products Group, AmericanHort Cultivate'23 2023, retrieved on Jun. 26, 2024 at https://heritageppg.com/blogs/pest-control-blog/cultivate-23-the-horticulture-event-of-the-year, 7 pp. (Year: 2023).*
Proven Winners Rise up Emberays Rose, retrieved on Jun. 26, 2024 at https://www.provenwinners.com/plants/rosa/rise-emberays-rose-rosa-x, 4 pp. (Year: 2024).*
YouTube Recovering and Rise Up Emberays Getting back out to the Garden! 2023 retrieved on Jun. 26, 2024 at https://www.youtube.com/watch?v=qd4So8sO29E, one page. (Year: 2023).*

* cited by examiner

*Primary Examiner* — June Hwu
(74) *Attorney, Agent, or Firm* — Cassandra Bright

(57) ABSTRACT

A new and distinct cultivar of *Rosa* plant named 'BOZFRA321' is disclosed, characterized by orange-pink semi-double flowers. Plants have semi-upright habits and are tolerant of high heat as well as rust and downy mildew. Flowers have an average diameter of 7 cm and a distinctive irregularly founded shape. The new variety is a shrub rose normally produced as an outdoor garden or container plant.

2 Drawing Sheets

Figure 1:
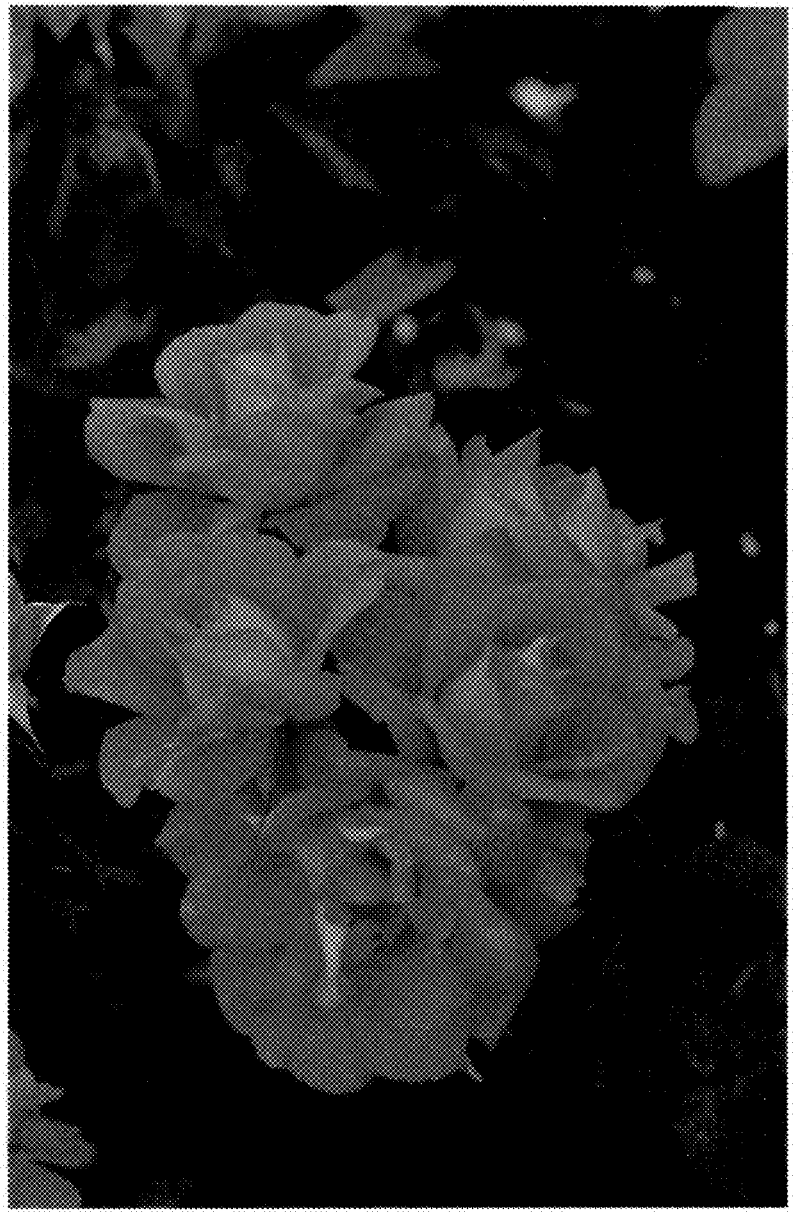

Latin name of the genus and species: *Rosa hybrida.*
Variety denomination: 'BOZFRA321'.

BACKGROUND OF THE INVENTION

The new *Rosa* cultivar is a product of a planned breeding program conducted by the inventor, Biljana Bozanic Tanjga, in Temerin, Serbia. The objective of the breeding program was to produce new profusely flowering shrub rose plants with good disease resistance. The cross resulting in this new variety was made during May of 2012.

The seed parent is *Rosa* 'POULJILL', U.S. Plant Pat. No. 12,522. The pollen parent is the unpatented *Rosa* 'Compassion'. The new variety was discovered in June of 2013 by the inventor in a group of seedlings resulting from the 2012 crossing, in a research nursery in Temerin, Serbia.

Asexual reproduction of the new cultivar was performed by softwood cuttings at a research nursery in Mali Idjos, Serbia in 2014, and has shown that the unique features of this cultivar are stable and reproduced true to type in multiple successive generations.

SUMMARY OF THE INVENTION

The cultivar *Rosa* 'BOZFRA321' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BOZFRA321'. These characteristics in combination distinguish 'BOZFRA321' as a new and distinct *Rosa* cultivar:

1. Orange-pink flowers.
2. Shrub rose with a semi-upright habit.
3. Tolerant to rust and downy mildew.
4. Very heat tolerant.
5. 7 cm average flower diameter.
6. Irregularly rounded shape of flowers; semi-double flower shape with a flat profile to the lower part and concave profile to upper section.

PARENTAL COMPARISON

Plants of the new cultivar 'BOZFRA321' are similar to plants of the seed parent in most horticultural characteristics, however, plants of the new cultivar 'BOZFRA321' differ in the following;

1. Plants of the new variety have an average height range of 90 to 110 cm; plants of the seed parent have an average height range of 100 to 150 cm.
2. Flowers of the new variety have on average 10 to 15 petals; flowers of the seed parent have on average 25 to 40 petals.

3. Flower diameter of the new variety is on average 7 cm; flower of the seed parent is on average 10 to 12 cm.
4. Flower color of the new variety is orange-pink, while the flower color of the seed parent is medium yellow.

Plants of the new cultivar 'BOZFRA321' are similar to plants of the pollen parent in most horticultural characteristics, however, plants of the new cultivar 'BOZFRA321' differ in the following;

1. Plants of the new variety have an average height range of 90 to 110 cm; plants of the pollen parent are about 150 cm in height.
2. Flower color of the new variety is orange-pink, while the flower color of the pollen parent is salmon-pink.
3. Flowers of the new variety have on average 10 to 15 petals; flowers of the pollen parent have on average 20 to 40 petals.
4. Flowers of the new variety have a weak fragrance, while flowers of the pollen parent have a strong fragrance.
5. Plants of the new variety have a shrub type habit, while plants of the pollen parent have a climbing habit.

COMMERCIAL COMPARISON

Plants of the new cultivar 'BOZFRA321' are comparable to the commercial variety *Rosa* 'Meigekanu', U.S. Plant Pat. No. 6,384. The two *Rosa* varieties are similar in most horticultural characteristics; however, the new variety 'BOZFRA321' differs in the following:

1. Flowers of the new variety are colored orange-pink while flowers of this comparator are colored vermillion to orange-red.
2. Plants of the new variety have an average height range of 90 to 110 cm; plants of this comparator average 150 to 165 cm in height.
3. Foliage of the new cultivar is green; foliage of this comparator is bronze-green.

Plants of the new cultivar 'BOZFRA321' are comparable to the commercial variety *Rosa* 'HARwelcome', U.S. Plant Pat. No. 9,161. The two *Rosa* varieties are similar in most horticultural characteristics; however, the new variety 'BOZFRA321' differs in the following:

1. Flowers of the new variety are colored orange-pink while flowers of this comparator are colored orange-apricot.
2. Plants of the new variety have an average height range of 90 to 110 cm; plants of this comparator average 75 to 150 cm in height.
3. Flower petal number of the new cultivar is on average 10 to 15; petal number this comparator is 25 to 30.
4. Flower diameter of the new variety is on average 7 cm; flower diameter of this comparator is on average 10 cm.

BRIEF DESCRIPTION OF THE PHOTOGRAPHS

The accompanying photograph in FIG. 1 illustrates in full color a typical inflorescence of 'BOZFRA321'.

Figure 2:
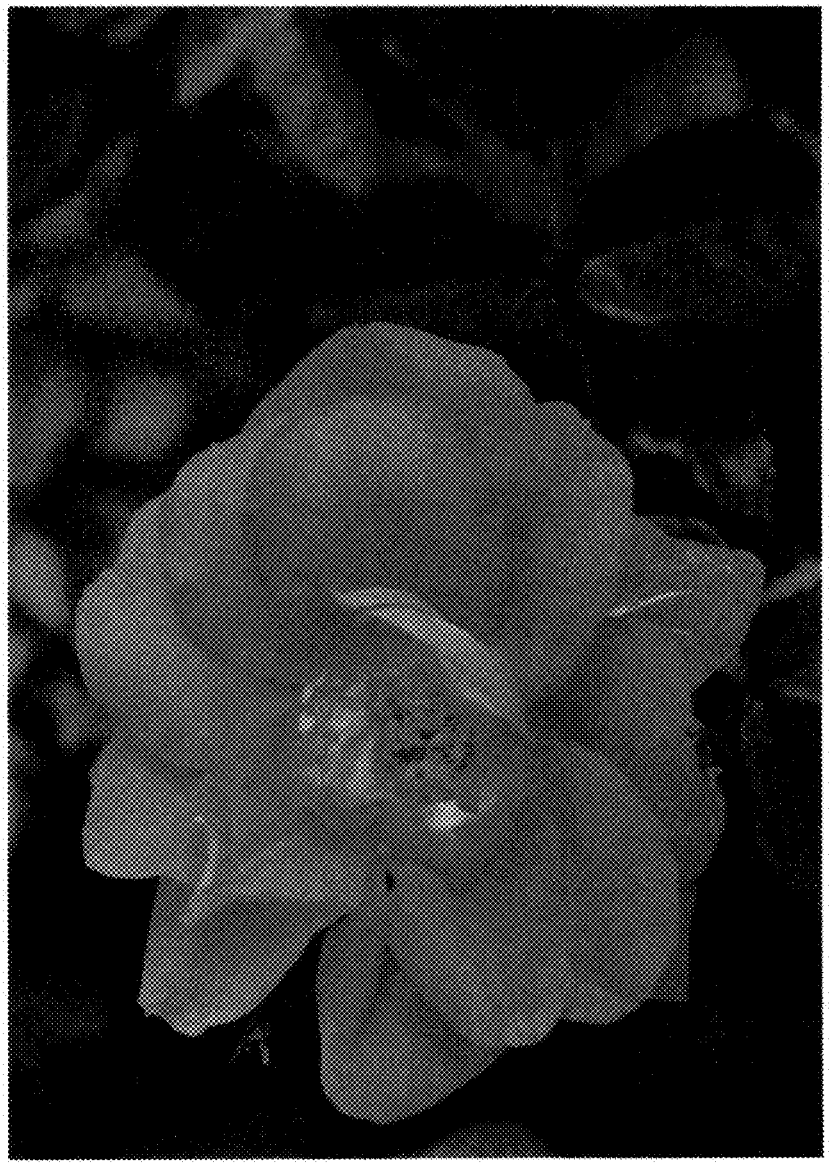

FIG. 2 illustrates a close-up view of a typical flower of 'BOZFRA321'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BOZFRA321' plants grown in the ground, outdoors during the Spring and Summer, in Mali Idios, Serbia. The growing temperature ranged from 15° C. to 36° C. during the day and from −25° C. to 23° C. during the night. General light conditions were bright, normal sunlight. No chemical treatments were used. Measurements and numerical values represent averages of typical plant types.
Botanical classification: *Rosa* 'BOZFRA321'.

PROPAGATION

Propagation method: Softwood cuttings.
Time to initiate roots: 30 days at 20° C. in summer.
Time to produce rooted plant: 120 days at 20° C. in summer.
Root description: Good density, moderately branched, medium thickness, fibrous, and fleshy. White in color, not accurately measured using R.H.S. chart.

PLANT

Age of plant described: Approximately 2 years old.
Plant type: Perennial shrub.
Rootstock: *Rosa corymbifera* 'Laxa'.
Growth habit: Upwards and slightly outwards.
Plant shape: Compact, upright.
Height: 90 to 110 cm.
Plant spread: About 60 cm.
Growth rate: Good.
Plant vigor: Fairly vigorous. About 1 year to reach 1.1 meter.
Branching characteristics:
Length of primary lateral branches: Approximately 90-110 cm.
Diameter of lateral branches: Approximately 0.6 cm.
Quantity of lateral branches: 3-4 main branches.
Branches-young wood:
- *Diameter.*—Approximately 0.4 cm.
- *Texture.*—Smooth.
- *Approximately density/quantity of thorns.*—5 to 10 along 10 cm of length.
- *Color.*—Near RHS Green 141D.

Branches-old wood:
- *Diameter.*—Approximately 0.8 cm, after 1 year.
- *Color.*—Near RHS Green 143C.
- *Texture.*—Smooth.
- *Approximately density/quantity of thorns.*—5 to 10 along 10 cm of length.
- *Thorns.*—Density: Moderate. Color: Near RHS Yellow-Green 147A. Height of thorns: 1.0 cm. Base diameter: 0.8 cm.

FOLIAGE

Leaf:
- *Arrangement.*—Alternate.
- *Quantity.*—2 along 10 cm of length of main branch.
- *Length.*—13.4 cm.
- *Width.*—10.8 cm.

Leaflet:
*Quantity.*—5 per leaf.
*Average length.*—4.4 cm.
*Average width.*—2.7 cm.
*Shape of blade.*—Elliptic.
*Apex.*—Acuminate.
*Base.*—Obtuse.
*Margin.*—Dentate. Absent or weak undulation.
*Texture of top surface.*—Smooth, leathery.
*Texture of bottom surface.*—Glabrous, leathery.
*Pubescence.*—None.
*Appearance.*—Moderately glossy on upper surface. Matte lower surface.
*Color.*—Young foliage upper side: RHS Green 143C. Young foliage under side: RHS Yellow-Green 144B. Mature foliage upper side: RHS Green 137A. Mature foliage under side: Near RHS Green 137C.
*Venation.*—Type: Pinnate. Venation color upper side: RHS Yellow-Green N144D. Venation color under side: RHS Yellow-Green N144D.

Petiole:
*Leaf.*—Length: 1.0 cm. Diameter: 1 mm. Color, upper surface: RHS Yellow-Green N144D. Color, lower surface: RHS Yellow-Green N144D. Texture: Smooth with small thorns.

Rachis:
*Leaf.*—Length: 3.4 cm. Diameter: 1 mm. Color, upper surface: RHS Yellow-Green N144D. Color, lower surface: RHS Yellow-Green N144D. Texture: Smooth with small thorns.

Stipules:
*Quantity.*—2.
*Shape.*—Linear/acicular.
*Apex.*—Acicular.
*Base.*—Fused along petiole.
*Margin.*—Entire.
*Length.*—22 mm.
*Width.*—8 mm.
*Texture.*—Smooth, both surfaces.
*Color, upper surface.*—RHS Yellow-Green 147A.
*Color, lower surface.*—RHS Yellow-Green N144D.

FLOWER

Natural flowering season: From the end of May until the end of September in Serbia.

Flower type and habit: Multiflora. 7 to 11 flowers per inflorescence.

Inflorescence size:
*Diameter.*—Approximately 13-24 cm.
*Height.*—Approximately 22 cm.

Flower form: Irregularly rounded, double flower with flat profile of lower part and concave profile of upper part.
*Diameter.*—Average 7 cm.
*Depth.*—3 cm.
*Persistent or self-cleaning.*—Self-cleaning.

Bud:
*Shape.*—Ovate.
*Length.*—2.8 cm.
*Diameter.*—1.4 cm.
*Color.*—RHS Red 47C.

Petals:
*Petal arrangement.*—
*Size.*—Length: 4.0 cm. Width: 3.2 cm.
*Shape.*—obovate.
*Margin.*—emarginated.
*Apex.*—shallow-emarginated.
*Base.*—
*Petal quantity.*—10-15.
*Texture.*—Silky and smooth.

Color:
Petals:
*When opening.*—Upper surface: Near RHS 47C. Lower surface: Near RHS Yellow-Orange 21B streaked and flushed Red 42B and 42C.
*Fully opened.*—Upper surface: Near RHS Red 47C lightly flushed 25B. Small basal spot near Yellow-Orange 17B. Lower surface: Near RHS Red 47D flushed Orange 24B. Small basal spot near Yellow-Orange 17A. Color Changes when aging: Fading to pink, near RHS Red 48D upper and lower surfaces.

Sepals:
*Arrangement.*—Whorl around base.
*Quantity.*—5.
*Shape.*—Triangular.
*Margin.*—Entire.
*Sepal extensions.*—Moderate.
*Apex.*—Acuminate. Medium sepal extensions.
*Base.*—Fused.
*Length.*—3.1 cm.
*Width.*—1 cm.
*Texture.*—Smooth, slightly pubescent on underside.
*Color.*—Upper side: RHS Green 138D. Under side: RHS Green 141D.

Peduncle:
*Length.*—6.2 cm.
*Diameter.*—2 mm.
*Angle.*—Upright, 75° to 90°.
*Strength.*—Strong.
*Texture.*—Slightly prickly/stubbly.
*Color.*—RHS Yellow-Green 144A.

Receptacle:
*Length.*—1.0 cm.
*Width.*—0.8 cm.
*Shape.*—Flat or nearly flat.
*Color.*—RHS Green-White 157D.

Fragrance: Weak.

REPRODUCTIVE ORGANS

Stamens:
*Number.*—About 105.
*Filament color.*—RHS Yellow 4B.

Anthers:
*Length.*—3 mm.
*Shape.*—Ovate.
*Color.*—RHS Orange 24A.
*Pollen.*—Moderate to abundant.
*Pollen color.*—RHS Yellow-Orange 17B.

Pistil:
*Number.*—About 73.
*Length.*—9 mm.
*Style.*—Length: 8 mm. Color: RHS Yellow-Green 149D.
*Stigma.*—Shape: Lobed. Color: RHS Green-White 157D.

OTHER CHARACTERISTICS

Seeds and fruits: Pitcher-shaped hips, orange when mature, 1.6 cm long and 1.8 cm wide.

Disease/pest resistance: Tolerant to rust (*Phragmidium mucronatum*) and downy mildew (*Peronospora sparsa*). No observed resistance or susceptibility to normal diseases and pests of garden roses.

Temperature tolerance: Observed tolerance between −25° C. to at least 36° C. degrees.

What is claimed is:

1. A new and distinct cultivar of *Rosa* plant named 'BOZFRA321' as herein illustrated and described.

* * * * *